United States Patent

Simmen et al.

[11] Patent Number: 5,636,985
[45] Date of Patent: Jun. 10, 1997

[54] DENTAL IMPRESSION TRAY

[75] Inventors: Christian Simmen, Mahwah, N.J.; Alan N. Miller, New City; Nathaniel H. Lenchner, Lake Success, both of N.Y.

[73] Assignee: Coltene/Whaledent Inc., Mahwah, N.J.

[21] Appl. No.: 448,036

[22] Filed: May 23, 1995

[51] Int. Cl.⁶ .................................................. A61C 9/00
[52] U.S. Cl. ............................ 433/37; 433/38; 433/71
[58] Field of Search ........................... 433/37, 38, 41, 433/47, 71, 48

[56] References Cited

U.S. PATENT DOCUMENTS

| | | |
|---|---|---|
| 1,360,146 | 11/1920 | Ragatz ........................ 433/41 |
| 1,584,092 | 5/1926 | Harris . |
| 1,979,493 | 11/1934 | Salvio . |
| 2,597,929 | 5/1952 | Gorsky et al. . |
| 2,634,500 | 4/1953 | McAdoo . |
| 3,085,337 | 4/1963 | Shulman . |
| 3,501,837 | 3/1970 | Clark . |
| 4,161,067 | 7/1979 | Bekey et al. ................ 264/16 X |
| 4,182,507 | 1/1980 | Bekey et al. ................ 264/16 X |
| 4,204,323 | 5/1980 | Neubert et al. ................ 433/38 |
| 4,251,209 | 2/1981 | Bekey et al. ................ 433/34 |
| 4,449,927 | 5/1984 | Taylor et al. ................ 433/38 |
| 4,602,905 | 7/1986 | O'Keefe, III ................ 433/41 |
| 4,619,610 | 10/1986 | Pelerin ................ 433/41 |
| 4,689,010 | 8/1987 | Wolfe ................ 433/38 |
| 5,336,086 | 8/1994 | Simmen et al. ................ 433/37 |

*Primary Examiner*—Nicholas D. Lucchesi
*Attorney, Agent, or Firm*—Helfgott & Karas, P.C.

[57] ABSTRACT

The modulus of elasticity and yield strength of a rigid core rod are set within predetermined limits as to limit the elastic deformation and prevent plastic deformation of a dental tray during multiple impression taking, bite registration and subsequent handling. The tray is formed with a frame which provides a positive recovery force when it is flexed. The cross section of the core rod may be optimized to further limit deflection in a predetermined plane. Various preferred materials including nonwoven spun-bonded filaments are selected for supporting impression material on the tray while minimizing the likelihood of obstructing a patient's teeth during full occlusion.

20 Claims, 2 Drawing Sheets

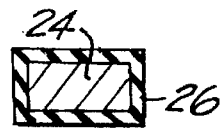
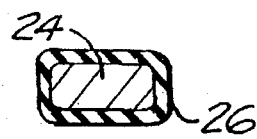
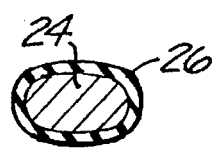
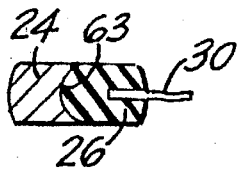
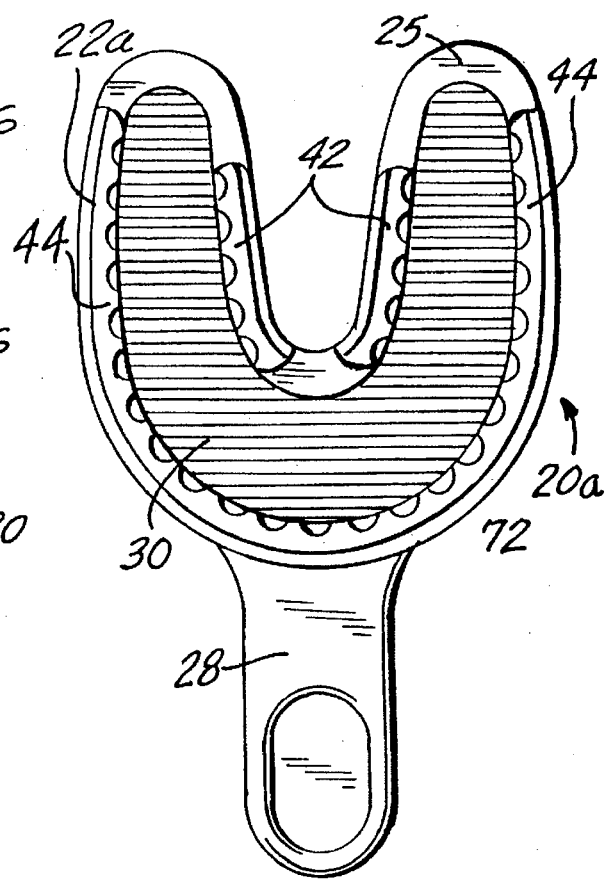
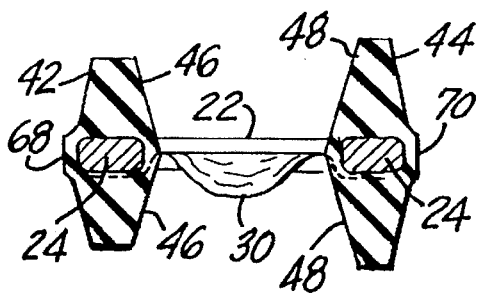
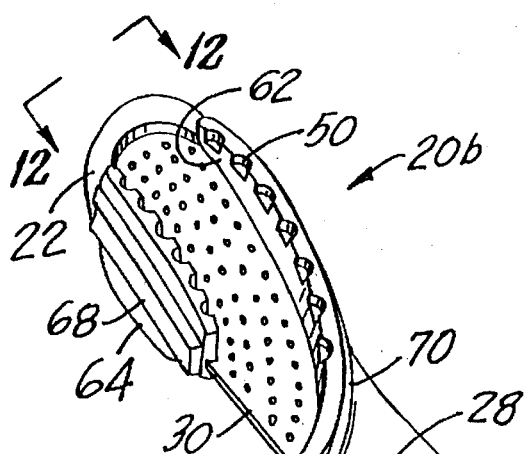
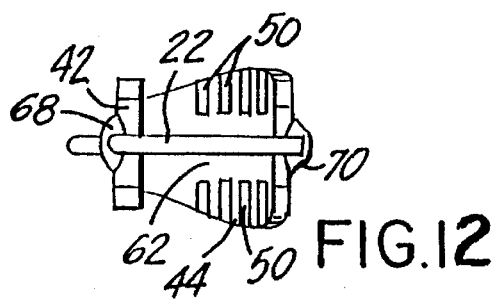

DENTAL IMPRESSION TRAY

BACKGROUND OF THE INVENTION

1. Field of the Invention

The present invention relates in general to an apparatus for forming impressions of a patient's teeth, gums and oral cavity and particularly relates to a dental tray having a rigid frame supporting a thin mesh or membrane for simultaneously making accurate impressions of a patient's upper and lower teeth as well as the bite registration therebetween.

2. Description of Prior Developments

Dental impression trays have long been used by dentists to form impressions of various portions of a patient's mouth and teeth. Such impressions are typically used to produce dental replacement components and dental assemblies such as crowns, teeth, bridgework, dentures and other oral prostheses.

One common type of dental impression tray is used to take an impression of either an upper or lower portion of the teeth and mouth by pressing a tray filled with impression material against that area of the mouth requiring repair or reconstruction.

Another type of dental impression tray, referred to herein as a multiple impression tray, is used to take impressions of both upper and lower portions of a patient's teeth and mouth and to concurrently provide an impression of the relative positions of the upper and lower teeth during a bite. The upper impression corresponds to an impression section of maxilla, the lower impression corresponds to a complimentary section of mandible and the two complimentary impressions jointly provide an impression of the bite relationship of mandible to maxilla.

A typical multiple impression tray includes an upper trough and a bottom trough, each filled with impression material such as a setable rubber base material. The tray is placed in a patient's mouth and the patient is instructed to bite into the impression material until the patient's upper and lower teeth substantially abut one another. During this procedure, the impression material is displaced and extruded between portions of the tray and the patient's teeth and gums.

The forces developed during this displacement and extrusion of the impression material have resulted in the formation of inaccurate and distorted impressions. That is, as the impression material is pressurized during biting, it presses against the frame of the multiple impression tray causing it to flex, bend and distort in shape. If the frame does not fully recover or if it takes a permanent set, for instance during manipulation for removal from mouth or in lab production (preparation and stone moldings) an inaccurate impression will likely result. This problem is particularly noticeable with those multiple impression trays formed of highly flexible material such as plastic or thin wire.

When a dental impression is taken with such a prior art impression tray, the bending and flexing of the frame can be further exacerbated as the tray is removed from the patient's mouth. Due to the forces required to free the patient's teeth from the impression material, the tray is again flexed and often spread open and twisted causing deformation and distortion of the impressions.

Even after an impression has been made, it may be subject to additional distortion in the laboratory. As a technician manipulates the impression tray while producing a mold, the tray is often again flexed or bent thereby causing the movement and relative displacement of the impression material.

Although some dental impression trays have been made of metal, the particular metal used has been in the form of easily deformed wire or easily flexed sheets which provide minimal rigidity against deformation and flexing. Moreover, such trays have been known to take a permanent set once they have been bent out of shape and therefore fail to return to their original shape. In this case, the impressions taken tend to be held in a deformed condition thereby yielding unsuitable impressions.

Another problem particularly applicable to multiple impression trays is the inability, in some cases, of the patient to bring the upper and lower teeth into full abutting contact due to the presence of an intervening layer of material which defines upper and lower troughs for receiving impression material. This intervening layer or membrane is required to support and hold the impression material in the upper and lower troughs of the impression tray.

The presence of this intervening material, even though it may be quite thin, can prevent the required contact between the upper and lower teeth and thereby prevent an accurate impression and reproduction of the patient's bite registration. The thicker the intervening material, the less likely will be the reproduction of an accurate bite registration between maxilla and mandible.

An example of such prior art support material is a gauze or a meshed material which provides support for the impression material yet also allows the impression material to flow across and through it, preferably from the upper trough to the lower or bottom trough. Even though this mesh or gauze material is relatively thin, it still can prevent the upper and lower teeth from meeting.

One prior conventional approach to solving this problem has been to use mesh material having wide spacings between adjacent filaments or strands. This wide spacing allows the teeth to spread the filaments apart and thereby meet between the filaments. This in turn allows full penetration of the impression material and accurate bite registration.

Another approach to solving this problem relies on the use of a nonwoven fabric material to support the impression material. This nonwoven fabric material is formed of staple fibers having predetermined lengths. As such, it is generally thick and dense and must be penetrated and pierced by the teeth.

When this material is pierced and sheared, its cut ends, which are taut, can fold into the impression cavity adjacent and between the teeth. These ends then extend into the impression cavity after removal from the patient's mouth and act as foreign objects in the resulting mold. This can result in a defective, deformed or substandard prosthetic molding.

Accordingly, a need exists for a dental impression tray which includes a rigid structure resistant to deflection, deformation and twisting during and after the formation of a dental impression.

A further need exists for a dental multiple impression tray which is formed of a rigid material and which resists plastic deformation during the forming of dental impressions.

A further need exists for a dental multiple impression tray which adequately supports a layer of impression material in both its upper and lower troughs, yet allows substantially free abutting contact between a patient's upper and lower teeth during the formation of a dental impression.

Still a further need exists for a dental multiple impression tray which substantially eliminates the need for piercing an intervening layer of material which supports impression material in the upper and lower troughs of the tray.

Yet a further need exists for a dental multiple impression tray which eliminates the presence of sheared filaments or strands extending into a dental impression cavity carried by the tray.

SUMMARY OF THE INVENTION

The present invention has been developed to fulfill the needs noted above and therefore has as an object the provision of a dental tray formed of a rigid material which resists deflection, deformation, flexing, bending and twisting during the formation of a dental impression.

Another object of the invention is the provision of a dental impression tray which resists bending, flexing and deformation during its removal from a patient's mouth and during subsequent handling during laboratory work.

Another object of the invention is the provision of a dental impression tray having a rigid frame which resists flexure and which also resists plastic deformation.

Another object of the invention is the provision of a dental impression tray which adequately supports a layer of impression material in its upper and lower troughs, yet which also allows virtually free unobstructed contact between a patient's upper and lower teeth.

Still another object of the invention is the provision of a dental impression tray which substantially eliminates the need for the piercing or shearing of an intervening layer of material during the formation of a bite registration impression.

Yet another object of the invention is the provision of a dental impression tray which provides accurate dental impressions free from deformities caused by flexure, twisting or bending of the frame which supports the impression material.

In order to carry out the objects noted above, a dental impression tray is constructed according to the present invention so as to limit its flexure and bending during and after the formation of a dental impression. Flexure and bending, as well as twisting and deformation of the tray, are controlled by constructing the frame of the tray with a relatively rigid material such as steel.

In particular, a rigid material such as steel is selected within a specified range of elastic moduli and yield strengths so as to control and limit the flexure of the impression tray, yet prevent the occurrence of plastic deformation. Even if some elastic deformation of the simultaneous impression tray takes place, for instance during the manipulation for removal from mouth or in lab production (stone molding and preparation) the rigid frame will quickly return to its original free state thereby preventing the distortion of the impression material adjacent a patient's teeth.

The cross sectional shape of the steel frame may be configured so as to maximize its resistance to flexure in a preferential direction. That is, the steel frame may be formed with a rectangular or elliptical section having a major dimension or axis extending within a plane within which the maximum bending force will be applied during bite registration.

The rigid frame may be provided in the form of a high elastic modulus core rod encapsulated in a plastic material. The plastic material not only adds to the aesthetics of the impression tray but also provides a softer contact surface for engagement with a patient's mouth and teeth.

Additional rigidity can be provided to the impression tray by molding a plastic support structure around the rigid core. This plastic support structure can include a pair of side walls which support and control the flow of impression material. The side walls can be shaped with grooves for receiving and anchoring the impression material within the tray. Additional rigidity may be provided in the form of plastic molded stiffening ribs.

In order to minimize the interference between the impression tray and the patient's teeth during the formation of a bite registration impression, the present invention adopts in one embodiment a spun-bonded, nonwoven fabric material for supporting the impression material within the upper and lower troughs of the impression tray. This spun-bonded fabric material is formed from multiple continuous filaments having average diameters less than about 0.0007 inch and loosely spread apart. As a result, it is typically not as dense and thick as fabrics made by other methods such as weaving, knitting, warpknitting and staple nonwovens, but yet still as strong.

Thus, when a patient bites through the impression material and into the spun-bonded filaments, it is less likely that the filaments will be sheared because of their smaller diameter and looser and easier spreading than nonwoven materials based on staple fibers. This spreading action prevents the formation of loose cut ends and thereby prevents such ends from causing nonconformities within the impression cavities.

The presence of loose cut ends can be further reduced by mounting the filamentary fabric of spun-bonded material to the frame of the impression tray in a loose or untensioned manner. In this case, even if a filament fiber is sheared, it will not be taut as in the case of a woven knitted or warp knitted material. Rather, the sheared end will be loose and untensioned and unable to project into the impression cavity.

Although a spun-bonded, continuous filament membrane functions well in this application, other membrane materials may be used provided they are selected within predetermined thickness limits. For example, a thin foil of silicone could be used, or a sheet of perforated or meshed tin, or metal foil, or individual threads oriented in a predetermined direction on the multiple tray frame.

The term membrane, as used to describe the support layer between the upper and lower troughs includes foils, fabrics and individual threads. Foils include metals such as tin and plastics such as silicone. Fabrics include nonwoven materials, woven, knitted and warp knitted material. Nonwoven materials include spun-bond materials, such as synthetics, and staple fibers which include natural and synthetic fibers.

Threads suitable for use as membrane 30 include continuous filaments such as monofilaments and preferably multifilaments. Examples of such multifilaments are man-made synthetic fibers. Other less suitable threads may be derived from staples which are fibers having a typical length of about 1 to 2½ inches. Staple fibers include natural fibers, synthetic fibers and blends of the two. Woven materials are not preferred for membrane 30.

Grooves provided for anchoring the impression material within the multiple impression tray are formed in such a manner that they do not extend across the full height of the sidewalls. Rather, the grooves extend toward the rigid core from the top and bottom portions of the sidewalls and end short of the core so as to define a plastic reinforcing rib surrounding the rigid core. This rib can extend partially or completely around the rigid core to resist flexure and twisting of the tray.

The aforementioned objects, features and advantages of the invention will, in part, be pointed out with particularity, and will, in part, become obvious from the following more detailed description of the invention, taken in conjunction with the accompanying drawings, which form an integral part thereof.

BRIEF DESCRIPTION OF THE DRAWINGS

In the drawings:

FIGS. 8(a), 8(b), 8(c), 8(d), 8(e) and 8(f) are views in cross section through various embodiments of a core rod according to the invention;

FIG. 9 is a view similar to FIG. 2 showing an alternate embodiment of the invention;

FIG. 10 is a top plan view of another embodiment of the invention in the form of a full arch multiple impression tray;

FIG. 11 is a perspective view of an alternate embodiment of the invention; and

FIG. 12 is an end view of FIG. 11 taken along line 12—12 thereof.

In the various figures of the drawings, like reference characters designate like parts.

DETAILED DESCRIPTION OF THE PREFERRED EMBODIMENTS

The present invention will now be described in conjunction with the drawings, beginning with FIG. 1 which depicts a dental impression tray 20 constructed in accordance with the invention. Tray 20 is adapted to simultaneously form an impression of at least a portion of a patient's upper teeth or maxilla and an impression of a complimentary portion of the patient's lower teeth or mandible. At the same time, the relative position or alignment of these upper and lower mating portions is established.

The relative alignment between the upper and lower teeth is known as bite registration. Since three useful measurements are provided during a single impression procedure, this type of dental impression tray is referred to as a simultaneous impression tray.

Figure 1:
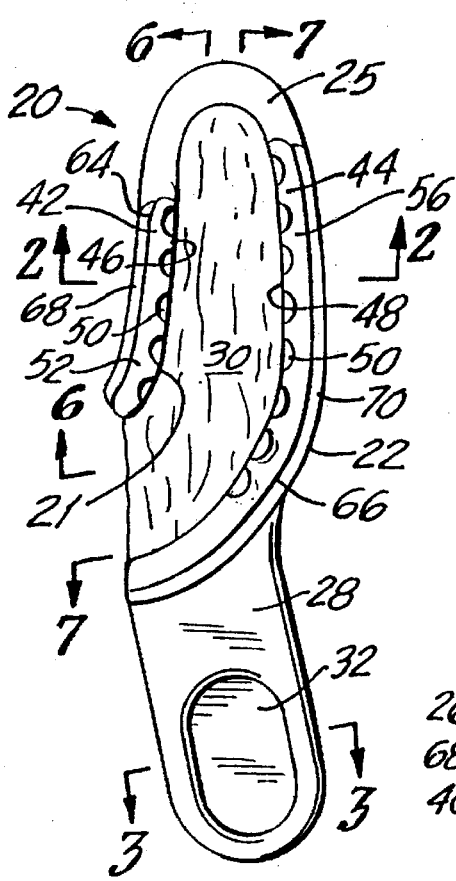
FIG. 1 is a top plan view of a posterior dental impression tray according to the invention.
Figure 2:
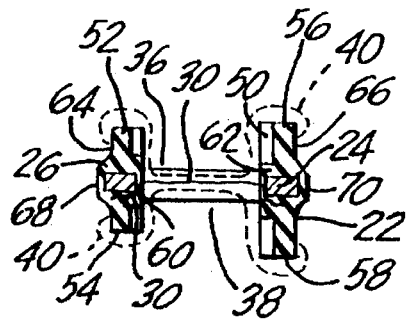
FIG. 2 is a view in partial section taken along line 2—2 of FIG. 1.

As further shown in FIGS. 1 and 2, tray 20 includes a composite frame 22 having a somewhat U-shaped configuration and formed of a relatively rigid central core rod 24 surrounded at least in part by a softer encapsulating material 26. Material 26, which may be a hard rubber or plastic material, is molded around core 24. Handle 28 (FIG. 1) may be molded from plastic material 26 at the same time that the material is molded around the central core 24. In addition, membrane 30 may be mounted to frame 22 during and by this molding operation by insert molding continuously around the membrane periphery.

The frame 22 includes at least a pair of legs 21,23 connected by an arcuate end portion 25 which together define a plane within which membrane 30 is supported. As discussed further below, frame 22 is designed so as to minimize deflection of legs 21 and 23 toward and away from one another within the above-noted plane.

Figure 3:
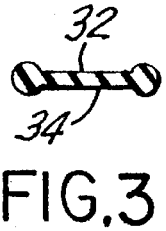
FIG. 3 is a view in section taken along line 3—3 of FIG. 1.

Membrane 30 is shown in FIG. 2 as being molded to the lower face of core 24, however, any suitable connection between membrane 30 and frame 22 is contemplated in accordance with the invention. Handle 28 may be molded with a pair of opposed recesses 32,34 as shown in FIG. 3 so as to provide a convenient grip between a dentist's thumb and index finger.

Frame 22 and membrane 30 define an upper trough 36 and a lower trough 38 for receiving and containing dental impression material 40 as shown in phantom in FIG. 2. The impression material 40 is coated over first and second opposed sidewalls 42,44 and membrane 30. Sidewalls are also molded from the plastic material 26 during the molding of frame 22. Although sidewalls are generally preferred, they are not always required for carrying out the invention.

Figure 4:
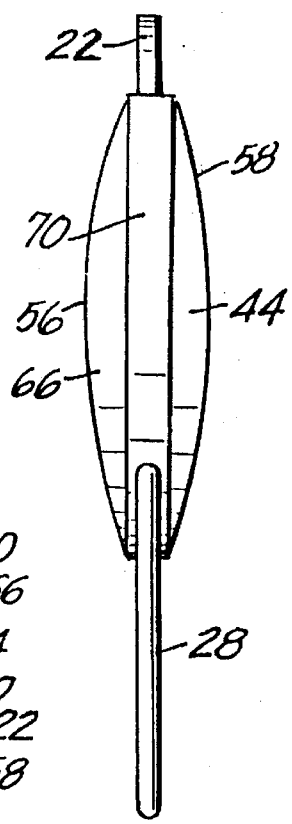
FIG. 4 is a right side elevation view of FIG. 1.
Figure 5:
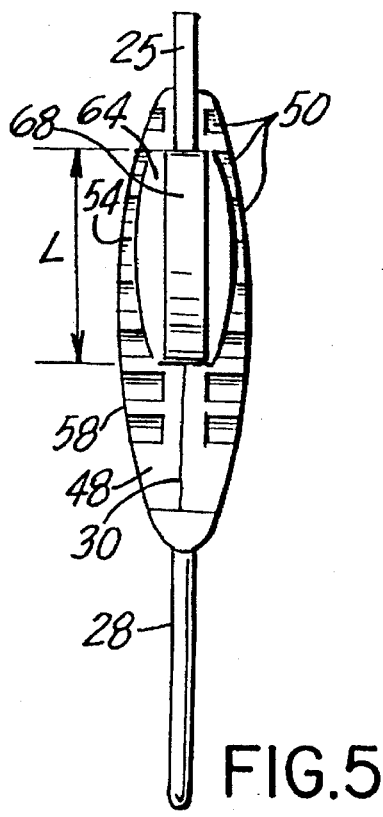
FIG. 5 is a left side elevation view of FIG. 1.
Figure 6:
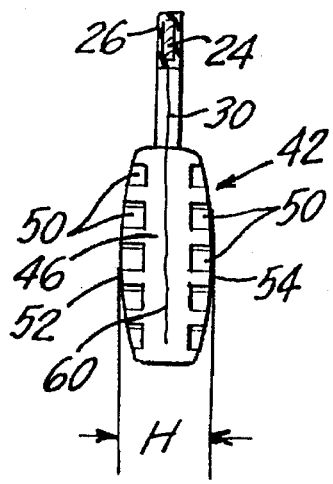
FIG. 6 is a view in partial section taken along line 6—6 of FIG. 1.

Each sidewall 42,44 respectively includes an inner face 46,48 having a plurality of cavities or recesses 50 formed therein. For the particular posterior form of simultaneous impression tray shown in FIGS. 1 through 7, and as best seen in FIGS. 4, 5 and 6, the first or inner sidewall 42 is both shorter in its length L and its height H than the corresponding length and height of the second or outer sidewall 44.

The first or inner sidewall 42 is bordered along its upper edge by a generally arcuate top wall 52 and along its lower edge by a generally arcuate bottom wall 54. In a similar fashion, the second or outer sidewall 44 is bordered along its upper edge by a generally arcuate top wall 56 and along its lower edge by a generally arcuate bottom wall 58. Walls 52 and 54 of sidewall 42 are disposed generally symmetrically about core 24 as are walls 56 and 58 of sidewall 44.

A series of longitudinally spaced cavities or recesses 50 extends from top wall 52 of inner sidewall 42 along its inner face 46 and from bottom wall 54 of inner sidewall 42 along its inner face 46 in general mutual alignment toward core 24. In similar fashion, a series of cavities 50 extends from top wall 56 of outer sidewall 44 along its inner face 48 and from bottom wall 58 of outer sidewall 44 along its inner face 48 in general mutual alignment.

As seen in FIG. 2, cavities 50 do not extend completely across the respective sidewall inner faces 46,48 but rather terminate before reaching the central core 24. In this manner, a first longitudinally extending rib 60 is defined along inner face 46 and a second longitudinally extending rib 62 is defined along inner face 48.

Central ribs 60 and 62 extend over and along the inner faces of core 24 which border the upper and lower troughs 36,38 in order to provide added rigidity and resistance against flexure and deformation of frame 22. Although semi-cylindrical cavities 50 are shown in the drawings as defining the central ribs 60,62 any form of recess may be used. Recesses 50 assist in the retention of the impression material 40 on the multiple impression tray 20 during the formation of a simultaneous impression and during removal of the triple tray from a patient's mouth.

A particularly significant aspect of the invention is the choice of material for core 24. Core 24 is designed so that it is essentially rigid at all times yet allows for a limited amount of elastic deformation during the formation of a simultaneous impression. It is important, however, to avoid any plastic deformation of the core and frame insofar as such plastic deformation will likely result in inaccurate and defective impressions.

The invention therefore provides a careful balance between the forces applied to the multiple impression tray during manipulation from removal from the mouth or in lab production (stone molding and preparation), and the elastic modulus and yield strength of the core material. In this manner, minor elastic deflection of the frame may take place with complete elastic recovery so as to maintain the impression material in close contact with the patient's teeth and gums without distortion or separation of the impression material from the patient's oral impression surfaces.

It has been found that the material of core 24 should be selected with an elastic modulus of at least 10 million pounds per square inch and a yield strength of at least 50 thousand pounds per square inch. Various metals such as steel alloys are particularly well suited for this application, such as stainless steel Type 301,302 and 304, for example.

Steel alloys having elastic moduli of at least 28 million pounds per square inch are readily available and particularly suited for fabricating core rod 24. Other metals, such as alloys of titanium and aluminum may be used for core 24. Moreover, core 24 may be fabricated from reinforced fiber materials such as carbon-carbon and aramid fibers.

In order to provide even greater rigidity and structural integrity to the impression tray, the cross section of core 24 is designed to provide the greatest resistance to bending and flexure in the plane defined by membrane 30. That is, core 24 is designed in such a manner so as to resist the relative movement of sidewalls 42 and 44 toward and away from one another so as to prevent distortion of the impression material during the formation of an impression. This in turn minimizes the flexure of the frame 22 toward and partially away from the sides of a patient's teeth during bite registration.

Figure 7:
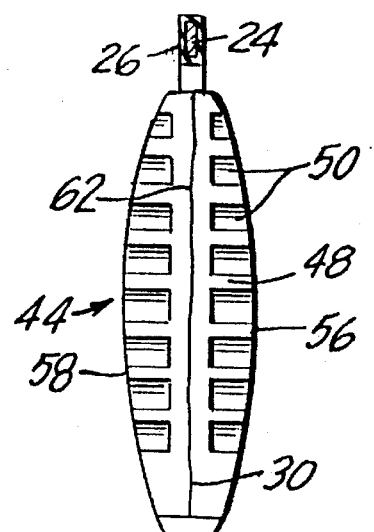
FIG. 7 is a view in partial section taken along line 7—7 of FIG. 1.

Referring again to FIG. 2, as well as to FIGS. 6 and 7, and particularly to FIG. 8(a), core 24 may be formed with a rectangular cross section having its major dimension or largest pair of sides extending generally parallel to a plane defined by the intersection of membrane 30 with frame 22. Stated another way, the major dimension of core 24 extends transverse to the sidewalls in a direction generally parallel and coplanar with a plane which separates the upper trough 36 from the lower trough 38 symmetrically with respect to frame 22 and core 24. The minor dimension of core 24 extends generally transverse to the plane of the membrane between the upper and lower troughs.

In this manner, the minor dimension or shortest sides of core 24 face one another across the gap between sidewalls 42,44 which define the sides of troughs 36,38. This orientation of the short sides or minor dimension extends generally transverse to the above-noted plane and membrane. This orientation of core 24 provides the greatest resistance to transverse bending of frame 22 toward and away from the sides of a patient's teeth during bite registration and reduces the chance of forming an inaccurate or distorted dental impression.

Alternate cross sections for core 24 taken for example through arcuate end portion 25, are shown in FIGS. 8(b), 8(c), 8(d), 8(e) and 8(f). FIG. 8(b) depicts a rectangular core 24 with chamfered edges. FIG. 8(c) depicts an oval or elliptical core 24 and FIG. 8(d) depicts a core with flat upper and lower surfaces interconnected by semi-circular sides. Other sections are of course possible. In some cases, even a round section is possible as shown in FIG. 8(e) if the limits on deflection and elasticity can be maintained.

Although FIGS. 8(a) through 8(e) all depict the arcuate end portion 25 of core rod 24 as being encapsulated or coated by a thin layer of plastic or elastomeric material 26, it is possible to leave the arcuate portion 25 uncoated except for its inner edge 63 which borders membrane 30, as shown in FIG. 8(f). Edge 63 of core rod 24 may be recessed or grooved to form an interlock between material 26 and core rod 24, with material 26 serving as an intermediary bonding member for securing membrane 30 to the core rod.

To add further rigidity to the multiple impression tray, a pair of external ribs may be molded to core 24 along the outer faces 64,66 of the inner and outer sidewalls 42,44. As seen in FIGS. 1, 2, 4 and 5, a first outer external rib 68 is molded around core 24 along outer face 64 of sidewall 42 and a second outer external rib 70 is molded around core 24 along outer face 66 of sidewall 44.

Another significant aspect of the invention is the selection of an appropriate material for membrane 30. As noted above, membrane 30 should provide adequate support for carrying a layer of impression material, yet present little or no obstacle to contact between a patient's teeth during bite registration. One suitable material for membrane 30 is a fabric made from nonwoven spun-bonded filaments. Such a fabric will function well if its overall or average thickness is maintained at or below about 0.003 inch as it forms membrane 30. Average thickness of fabrics chosen for membrane 30 should be measured according to ASTM-D-1777-64 standards.

This spun-bonded filament may be advantageously maintained within a weight to area ratio of no greater than 0.4 ounce per square yard as it extends between sidewalls 42,44. In order to ensure an adequate spacing between the fibers of the filament, its air permeability between the upper and lower troughs 36,38 should be greater than about 1100 cubic feet per minute per square foot as measured according to ASTM-D-737-75 standards. When membrane 30 is constructed of such a material, it resembles a fine gauze-like, translucent, gossamer membrane.

Examples of suitable fabrics include two CEREX fabrics respectively having fabric weights of 0.3 and 0.4 ounce per square yard, average thicknesses of 2.6 and 2.9 mils, burst strengths of 9 and 12 psi, and air permeabilities of 1330 and 1110 cubic feet per minute per square foot according to standard ASTM-D-737-75.

Although the spun-bonded filamentary membrane which forms membrane 30 in FIGS. 1 through 7 is held on frame 22 in a somewhat flattened state, it may also be loosely held on frame 22 as shown in FIG. 9. By loosely mounting membrane 30 to frame 22 in the manner of a loose net, membrane 30 will present virtually no resistance to deformation between the interengaged surfaces of a patient's teeth during bite registration.

FIG. 9 also depicts a modification to the inner faces 46 and 48 of sidewalls 42 and 44 in that these faces diverge outwardly from frame 22. This facilitates bite registration by guiding or wedging the teeth toward membrane 30.

Another possible construction of membrane 30 is an array of yarn in the form of continuous filaments spanning across the multiple impression tray. An example of such an arrangement is shown in FIG. 10 in the context of a full arch multiple impression tray 20(a). A series of parallel spaced multifilament yarns 72 is strung across frame 22(a). Twenty to forty strands may be used in the embodiment of FIG. 10 and ten to twenty strands with the embodiment of FIG. 1.

Threads 72 are preferably chosen as multifilament with all the filaments together having a value of less than about 2.0 tex wherein 1.0 tex equals one gram per one thousand meters in length. A pre-oriented yarn with a draw ratio of 1:1.3 to 1:3.5 has proven effective.

Instead of filaments, a perforated or continuous sheet of silicone-based film having an average thickness of about 0.001 inch to 0.002 inch may be used to form membrane 30. Alternatively, a foil of highly malleable metal, either continuous or perforated, having a thickness of about 0.0005 inch to 0.001 inch may be used to form membrane 30. An example of such a perforated silicone sheet or perforated metal foil is shown in FIG. 11 wherein membrane 30 is mounted to a posterior tray 20(b) virtually identical to tray 20 of FIG. 1. FIG. 12 provides additional details of trays 20 and 20(b).

There has been disclosed heretofore the best embodiment of the invention presently contemplated. However, it is to be understood that various changes and modifications may be made thereto without departing from the spirit of the invention.

What is claimed is:

1. A dental impression tray, comprising:

a rigid frame comprising a rigid core rod defining a generally U-shaped portion; and a membrane supported on and integral with said frame and spanning said U-shaped portion;

said rigid core having a cross section having a major dimension extending along said membrane and a minor dimension extending substantially transverse to said membrane, said rigid core rod comprising a predetermined modulus of elasticity and a predetermined yield strength, said modulus of elasticity and said yield strength selected to allow limited elastic deformation of said core rod during formation of a dental impression and said modulus of elasticity and said yield strength further selected to prevent plastic deformation of said core rod during said formation and handling of said dental impression.

2. The tray of claim 1, further comprising an inner sidewall and an outer sidewall each molded to said frame on opposite sides of said U-shaped portion.

3. The tray of claim 1, wherein said membrane comprises a fabric made from spun-bonded filaments.

4. The tray of claim 1, wherein said core rod comprises a metal rod comprising a modulus of elasticity of at least 10 million pounds per square inch.

5. The tray of claim 4, wherein said core rod further comprises a yield strength of at least 60 thousand pounds per square inch.

6. The tray of claim 4, wherein said core rod comprises a cross section having a major dimension and a minor dimension.

7. The tray of claim 1, wherein said core rod further comprises a modulus of elasticity of at least 28 million pounds per square inch.

8. A dental impression tray, comprising:

a rigid frame comprising a rigid core rod at least partially encapsulated in a plastic material;

a membrane supported on said frame and forming with said frame an upper trough and a lower trough;

a pair of sidewalls supported on said frame on opposite sides of said membrane;

said rigid core rod comprising a cross section having a major dimension extending generally transverse with respect to said sidewalls and a minor dimension extending generally transverse to said membrane.

9. The tray of claim 8, wherein said rigid core rod comprises a metal rod having a modulus of elasticity of at least ten million pounds per square inch.

10. The tray of claim 8, wherein each one of said sidewalls comprises a plurality of aligned recesses disposed so as to define a central rib extending along said frame adjacent said rigid core rod.

11. The tray of claim 8, wherein said membrane comprises a filamentary membrane having an average thickness of no greater than about 0.003 inch.

12. The tray of claim 11, wherein said membrane is loosely mounted to said frame in an untensioned state.

13. The tray of claim 8, wherein said inner and outer sidewalls each comprises an outer face and wherein said frame comprises an external rib molded along each said outer face adjacent said rigid core rod.

14. The tray of claim 8, wherein said rigid core rod comprises a rectangular cross section.

15. The tray of claim 8, wherein said rigid core rod comprises an oval cross section.

16. A dental tray, comprising:

a frame having at least a pair of legs connected by an end portion; and a thin membrane mounted between said legs, said membrane being made from spun-bonded continuous filaments of predetermined length comprising an average thickness of no greater than 0.003 inch, such that said membrane can carry a layer of impression material but present little or no obstacle between patient's teeth during bite registration.

17. The tray of claim 16, wherein said membrane comprises a weight to area ratio of no greater than 0.4 ounce per square yard and wherein said membrane comprises an air permeability of greater than 1100 cubic feet per minute per square foot.

18. The tray of claim 16, wherein said membrane is mounted on said frame in a loose untensioned configuration.

19. The tray of claim 16, wherein said membrane comprises a plurality of multifilament yarns strung mutually parallel between said legs.

20. A dental impression tray of claim 16 wherein said spun-bonded filaments are synthetic fibers.

* * * * *